(12) United States Patent
Reissmann et al.

(10) Patent No.: US 6,184,345 B1
(45) Date of Patent: Feb. 6, 2001

(54) BRANCHED BUILDING UNITS FOR SYNTHESIZING CYCLIC PEPTIDES

(75) Inventors: Siegmund Reissmann; Bettina Müller, both of Jena; Peter Kleinwächter, Gera; Diana Besser, Jena, all of (DE)

(73) Assignee: Peptor Limited, Rehovot (IL)

( * ) Notice: Under 35 U.S.C. 154(b), the term of this patent shall be extended for 0 days.

(21) Appl. No.: 09/246,567

(22) Filed: Feb. 8, 1999

Related U.S. Application Data

(63) Continuation-in-part of application No. 08/990,591, filed on Dec. 15, 1997, now abandoned.

(51) Int. Cl.⁷ .................................................. C07K 5/02
(52) U.S. Cl. .......................... 530/323; 530/332; 530/333
(58) Field of Search ...................................... 530/323, 332

(56) References Cited

U.S. PATENT DOCUMENTS 5,723,575  3/1998  Gilon et al. ........................... 530/317

OTHER PUBLICATIONS

Eldrup, A. et al. J. Amer. Chem. Soc., 119 (45), 11116–11117, Nov. 1997.*
G. Byk et al., *J. Org. Chem.*, 1992, 57:5687–5692.
Kaljuste et al., *Int. J. Peptide Protein Res.*, 1994, 43:505–511.
S. Reissmann et al., *Biomedical Peptides, Proteins & Nucleic Acids*, 1994,1 :51–56.
R. Zuckermann et al., *J. Am. Chem. Soc.*, 1992, 114:10646–10647.

* cited by examiner

*Primary Examiner*—Michael Borin
(74) *Attorney, Agent, or Firm*—Pennie & Edmonds LLP

(57) ABSTRACT

The present invention relates to building units suitable for the synthesis of backbone cyclized peptides. The building units of this invention have structures of Formula (I):

$$X-AA_m-U-AA_p-Y \qquad (I)$$

wherein $AA_m$ and $AA_p$ are residues of natural or synthetic amino acids and U is $C^\alpha ON[(CH_2)_{n+1}W]$ or $\Psi(C^\alpha H_2N)[CO(CH_2)_q W]$, in which $C^\alpha$ is a carbon atom and is the α carbon of $AA_m$ if m>0. W is NH—X or COY, and X is H, Boc, Z, Fmoc, or Alloc while Y is the hydroxyl group of a carboxylic acid moiety or a carboxylic acid protecting group. The letter m refers to an integer from 0 to 10; n is a number from 0 to 6; p is a number from 1 to 10; and q is a number from 1 to 6. The present invention is also directed to methods of synthesizing building units of Formula (I) via different routes.

11 Claims, No Drawings

BRANCHED BUILDING UNITS FOR SYNTHESIZING CYCLIC PEPTIDES

CROSS-REFERENCE TO RELATED APPLICATIONS

This application is a continuation-in-part of U.S. patent application Ser. No. 08/990,591 filed Dec. 15, 1997 now abandoned.

TECHNICAL FIELD

The present invention relates to a method for preparing branched building units for use in the synthesis of backbone cyclized peptides, and to the building units themselves.

BACKGROUND OF THE INVENTION

Biologically active peptides are conformationally restricted through cyclization to achieve metabolic stability, to increase potency, to confer or improve receptor selectivity, and to control bioavailability. The use of medium and long-range cyclization to convert natural bioactive peptides into potential peptidomimetic drugs has been prompted by the ability to control these important pharmacological characteristics. Furthermore, the structural constraints on a peptide brought about by cyclization also enhance conformational homogeneity and facilitate conformational analysis. See, e.g., Kessler, H. *Angew. Chem. Int. Ed. Eng.* 21:512 (1982). Thus, cyclization may give insight into the biologically active conformations of linear peptides provided that their biological activities and selectivities are maintained.

Common modes of long-range (or global) peptide cyclization include side-chain to side-chain, end-group to end-group, and side-chain to end-group, all of which require the alteration or removal of residue side chains. See, e.g., Manesis, N. J., and Goodman, M. *Org. Chem.* 52:5331 (1987). Backbone cyclization, wherein a connection is made between the $N^\alpha$ and/or $C^\alpha$ atoms of a peptidic backbone, does not require such disruption of the peptide's natural structure because only the hydrogens of the peptide bond are affected. The hydrogens are replaced by ω-functionalized chains that can be interconnected, connected to residue side-chains, or connected to the ends of a peptide to form the desired cyclic peptide. Backbone cyclization can thus stabilize a peptide's bioactive conformation and protect against its enzymatic degradation without altering its side chains.

Although different methods of backbone cyclization exist, a preferred method uses dipeptide building blocks. Gilon and coworkers have disclosed backbone to side-chain and backbone to C-terminus peptide cyclization using lactam and disulfide bridges formed from such building blocks. This was done with the use of N-aminoalkyl amino acids obtained either by the alkylation of amino, carboxy or thiol alkyl amines with triflates of α-hydroxy acids, or by the nucleophilic substitution of alkylene diamines. U.S. Pat. No. 5,723,575 and Gilon et al., *J. Org. Chem.* 57: 5687–5692 (1992) (collectively "Gilon").

In the first method of synthesizing N-aminoalkyl amino acids, a diamine is reacted with an α bromo acid to provide an ω amine which is then selectively protected. Variation of the protecting group provides a building unit suitable for Boc chemistry peptide synthesis. In the second method of synthesizing these building units, a selectively protected diamine is reacted with chloroacetic acid to provide a protected glycine derivative suitable for Fmoc peptide synthesis.

In order to take advantage of the facile nucleophilic displacement of carboxylic acid substituents, both synthetic methods described by Gilon require the reaction of a molecule of formula Halides-CH(R)—CO—OR' (wherein Halides represents a halogen leaving group) and an amine. The amine bears an alkylidene chain that is terminated by another amine, as shown in Scheme (I):

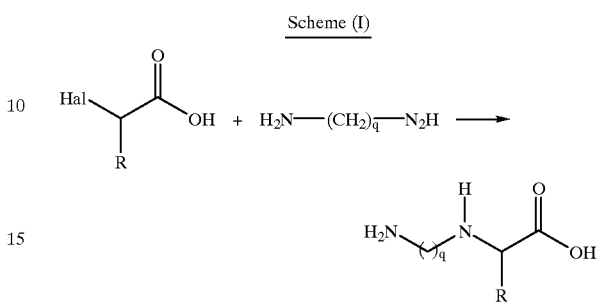

Scheme (I)

The terminating nitrogen atom of the resulting building unit will be contained by the moiety used to form the bridging chain of a cyclized peptide.

In a molecule where R is other than hydrogen, there is a high tendency to eliminate H-Halides under basic conditions. And because the secondary amine formed by the addition reaction is a better nucleophile than the primary amine of the diamine reactant, double alkylation products may form. This side reaction reduces the yield of the method shown in Scheme (I) to such an extent that it cannot be used for the practical production of building units based on amino acids other than glycine. Gilon, however, does not suggest backbone cyclization building units having end-group moieties that are not amine, and so only provides compounds useful in backbone to side-chain and backbone to C terminus peptide cyclization.

Other workers have described alternative backbone cyclization building blocks. For example, lactam bridges have been formed with the protected building block HN(CH$_2$COOBu$^t$)Phe, although the synthesis of bradykinin analogues using the Boc protected building block was reportedly hindered by low yields and undesired double couplings. Reissman et al. *Biomedical Peptides, Proteins & Nucleic Acids* 1:51–6 (1994). Increased efficiency was obtained, however, when the protecing group N,O-bis (trimethylsilyl)-acetamide was used. The cyclic peptides made with the building block, which contain N-alkylamide bonds, were reported to be unstable under acidic conditions typical of solid phase peptide synthesis.

The synthesis of backbone cyclized peptides using glycine-based building blocks has also been reported by Zuckermann et al. *J. Am. Chem. Soc.* 114: 10646–10647 (1994). This synthetic approach, which is limited to the solid phase preparation of N-substituted glycine oligomers consists of two steps: first, a resin bound secondary amine is alkylated; and second, a side-chain is introduced into the polypeptide by nucleophilic displacement of a halogen with an excess of a primary amine.

A more general method for the synthesis of backbone cyclized peptides is disclosed by Kaljuste et al. *Int. J. Peptide Protein Res.* 43: 505–511 (1994). By utilizing amino acid aldehydes, this method allows the formation of branched building units on a solid support, but requires that both the backbone and the branching chain of the resulting cyclic peptide contain reduced peptide bonds. The method is further limited by synthetic and storage problems associated with amino acid aldehydes, the relatively slow rates of alkylation of the reduced peptide bonds formed during the reaction, and the residue formed from sequence-specific side reactions that can occur during the reductive alkylation of reduced peptide bonds. Additional purification and racemization problems are also reported.

As made clear above, methods of peptide backbone cyclization have been constrained by the limited variety of building blocks. For example, the use of similar building block protecting groups can form hydrophobic clusters along the side chains of a growing peptide which can reduce coupling rates, reaction efficiencies and yields. Furthermore, some protecting groups can cause the racemization of terminal amino acids during the synthesis of a cyclic peptide. A third drawback of many building blocks is that cyclic structures formed from them degrade under the acidic and/or basic conditions typical of solid phase synthetic methods.

There thus exists a need for a larger variety of building units suitable for the synthesis of cyclic peptides, and a facile and efficient method of synthesizing such building units. There further exists a need for building units that are stable under solid phase synthetic conditions.

SUMMARY OF THE INVENTION

Accordingly, the present invention relates to building units suitable for the synthesis of backbone cyclized peptides. The building units of this invention have structures of Formula (I):

$$X—AA_m—U—AA_p—Y \quad (I)$$

wherein $AA_m$ and $AA_p$ are residues of natural or synthetic amino acids. U refers to $C^\alpha ON[(CH_2)_{n+1}W]$ or $\Psi(C^\alpha H_2 N)[CO(CH_2)_q W]$, in which $C^\alpha$ is a carbon atom and is the a carbon of $AA_m$ if m>0, with respect to N. W is NH—X or COY, and X is H, Boc, Z, Fmoc, or Alloc while Y is the hydroxyl group of a carboxylic acid moiety or a carboxylic acid protecting group. The letter m refers to an integer from 0 to 10; n is a number from 0 to 6; p is a number from 1 to 10; and q is a number from 1 to 6. The present invention also is directed to methods of making building units of Formula (I).

The invention more specifically is directed to a method of synthesizing building units of Formula (II):

$$X—AA_m C^\alpha ON[(CH_2)_{n+1}—W]AA_p—Y \quad (II)$$

wherein n is a number from 0 to 6. According to this method, a first reaction mixture comprising a compound of Formula (d) is prepared:

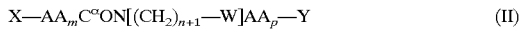

Formula (d)

wherein E is a carboxyl protecting group. This reaction mixture is then reacted with a compound of Formula (e):

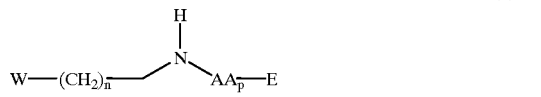

Formula (e)

wherein Halides is a halogen, under reaction conditions sufficient to form a second reaction mixture comprising the building unit of Formula (II). The building unit of Formula (II) may then be isolated from the second reaction mixture.

The present invention also encompasses a method of synthesizing a building unit of Formula (III):

$$X—AA_m\Psi(C^\alpha H_2 N)[CO(CH_2)_q—W]AA_p—Y \quad (III)$$

wherein q is a number from 1 to 6. According to this method, a first reaction mixture comprising a compound of Formula (m) is prepared:

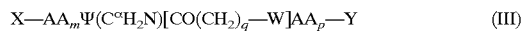

Formula (m)

wherein E is a carboxyl protecting group. This reaction mixture is then reacted with a compound of Formula (n):

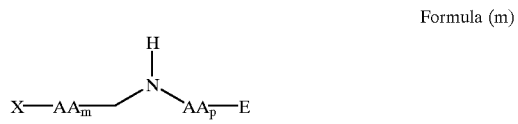

Formula (n)

under reaction conditions sufficient to form a second reaction mixture comprising the building unit of Formula (III). The building unit of Formula (III) may then be isolated from the second reaction mixture.

DETAILED DESCRIPTION OF THE PREFERRED EMBODIMENTS

All abbreviations used are in accordance with the IUPAC-IUB recommendations on Biochemical Nomenclature (*J. Biol. Chem.* 260:14–42 (1983)) and later supplements.

As used herein the term "amino acid" is intended to include any natural or synthetic amino acid. Abbreviations of typical amino acids used in the present invention are provided in Table (I):

TABLE I

| Amino Acids | |
|---|---|
| Abbreviated Designation | Name |
| Abu | α-Amino butyric acid |
| Ala | L-Alanine |
| Arg | L-Arginine |
| Asn | L-Asparagine |
| Asp | L-Aspartic acid |
| β Asp (Ind) | β-Indolinyl aspartic acid |
| Cys | L-Cysteine |
| Glu | L-Glutamic acid |
| Gln | L-Glutamine |
| Gly | Glycine |
| His | L-Histidine |
| Hyp | trans-4-L-Hydroxy Proline |
| Ile | L-Isoleucine |
| Leu | L-Leucine |
| Lys | L-Lysine |
| Met | L-Methionine |
| Nal | β-Naphthyl alanine |
| Orn | Ornithine |
| Phe | L-Phenylalanine |
| Pro | L-Proline |
| Ser | L-Serine |

TABLE I-continued

Amino Acids

| Abbreviated Designation | Name |
| --- | --- |
| Thr | L-Threonine |
| Trp | L-Tryptophane |
| Tyr | L-Tyrosine |
| Val | L-Valine |

Abbreviations of typical protecting groups, coupling agents, reagents and solvents suitable for use in the present invention are provided in Tables II–IV below. One skilled in the art will understand that the use assigned to each group of compounds is only a common use, and is not intended to limit the ways in which any particular compound may be employed. For example, a compound listed under "reagents and solvents" may be used as a protecting group. Furthermore, it is to be understood that other possible protecting groups, coupling agents, reagents and solvents suitable for use in the present invention are intended to be within its scope.

Abbreviations of protecting groups suitable for use in the present invention are provided in Table (II):

TABLE II

Protecting Groups

| Abbreviated Designation | Name |
| --- | --- |
| Ada | Adamantane acetyl |
| Alloc | Allyloxycarbonyl |
| Allyl | Allyl ester |
| Boc | tert-butylosycarbonyl |
| Bu$^t$ | tert-butyl |
| Bzl | Benzyl |
| Fmoc | Fluorenylmethyloxycarbonyl |
| OBzl | Benzyl ester |
| OEt | Ethyl ester |
| OMe | Methyl ester |
| pixyl | 9-phenylxanthen-9-yl |
| Tos (Tosyl) | p-Toluenesulfonyl |
| Trt | Triphenylmethyl |
| Z | Benzyloxycarbonyl |

As used herein, the term "coupling agent" refers to any compound or mixture of compounds that facilitates the coupling of two or more compounds. Abbreviations of coupling agents used herein are provided in Table (III):

TABLE III

Coupling Agents

| Abbreviated Designation | Name |
| --- | --- |
| BOP | Benzotriazol-1-yloxytris (dimethyl-amino) phosphonium hexafluorophosphate |
| DIC | Diisopropylcarbodiimide |
| HBTU | 2-(1h-Benzotriazol-1-yl)-1,1,3,3-tetramethyluronium hexafluorophosphate |
| PyBrOP ® | Bromotripyrrolidinophosphonium hexafluorophosphate |
| PyBOP ® | Benzotriazol-1-yl-oxy-tris-pyrrolidino-phosphonium hexafluorophosphate |
| TBTU | O-(1,2-dihydro-2-oxo-1-pyridyl)-N,N,N',N'-tetramethyl-uronium tetrafluoroborate |

Abbreviations of reagents and solvents suitable for use herein are provided in Table (IV):

TABLE IV

Reagents and Solvents

| Abbreviated Designation | Name |
| --- | --- |
| ACN | Acetonitrile |
| AcOH | Acetic acid |
| Ac$_2$O | Acetic acid anhydride |
| AdacOH | Adamantane acetic acid |
| Alloc-Cl | Allyloxycarbonyl chloride |
| Boc$_2$O | Di-tert butyl dicarbonate |
| DCM | Dichloromethane |
| DMA | Dimethylacetamide |
| DMF | N,N-dimethylformamide |
| DIEA | Diisopropylethylamine |
| Et$_3$N | Triethylamine |
| EtOAc | Ethyl acetate |
| Fm | Formyl |
| FmocOSu | 9-fluorenylmethyloxy carbonyl N-hydroxysuccinimide ester |
| HOBT | 1-Hydroxybenzotriazole |
| HF | Hydrofluoric acid |
| Me | Methyl |
| MeOH | Methanol |
| Mes (Mesyl) | Methanesulfonyl |
| NMP | 1-methyl-2-pyrrolidinone |
| nin. | Ninhydrin |
| i-PrOH | Iso-propanol |
| Pip | Piperidine |
| PP | 4-pyrrolidinopyridine |
| Pyr | Pyridine |
| TEA | Triethylamine |
| TFA | Trifluoroacetic acid |
| THF | Tetrahydrofuran |
| Triflate (Trf) | Trifluoromethanesulfonyl |
| Trf$_2$O | Trifluoromethanesulfonic acid anhydride |

As used herein, the term "reaction conditions" refers to conditions under which a chemical reaction may occur, and includes, for example, temperature, time, pressure, catalysts, co-catalysts, solvent, and other variables known to those skilled in the art.

As used herein, the terms "building unit," "building block," "peptide building unit," and "peptide building block" refer to a protected or unprotected compound that contains a moiety which may be incorporated into a peptide or peptide mimetic.

As used here, the terms "stable compound" or "stable structure" refer to a compound that does not undergo substantial decomposition under peptide synthesis conditions.

Because many of the compounds described herein have asymmetric centers, all chiral, diastereomeric, and racemic forms of them are included in the present invention. Many geometric isomers of olefins and the like can also be present in the compounds described herein, and all such stable isomers are contemplated by the present invention.

When any variable, such as X or Y, occurs more than once in any formula herein, its definition in each occurrence is independent of its definition at every other occurrence.

The present invention encompasses building units that enable the backbone cyclization of peptides. Unlike those of the prior art, the building units of this invention typically comprise carboxyl and/or an amino groups sterically hindered only by a branching moiety. In this way, the slow coupling rates typical of prior art building blocks containing, for example, N-alkyl groups may be avoided. An additional advantage of the building units of this invention is that they are easily purified via conventional extraction, precipitation and flash chromatographic means. Furthermore, the building units of the present invention are stable under both acidic and basic conditions, as well as in trimethylsilyl bromide solutions.

The branched peptide building units of the present invention are preferably formed by one of two methods: the acylation of N-aminoalkyl- or N-carboxyalkyl amino acids, or the acylation of protected pseudopeptides comprising reduced peptide bonds. In general, the individual procedures used to construct the branched peptide building units of this invention rely upon known principles of peptide synthesis, and upon solid phase peptide synthesis in particular. See, e.g., Bodanszky, *Principles of Peptide Synthesis* (Springer-Verlag: 1984); Bodanszky et al. *The Practice of Peptide Synthesis* (Springer-Verlag: 1984); Barany and Merrifield *The Peptides: Analysis, Synthesis and Biology* Vol. 2, Chapter 1 (Academic Press: 1980); Atherton et al. *Bioorg. Chem* Vol. 8 (1979). For example, synthesis of the compounds of this invention may utilize coupling agents such as those listed above. More novel coupling agents, such as pre-formed urethane-protected N-carboxy anhydrides (UNCA's) and pre-formed acyl fluorides, may also be used. Coupling reactions may occur at room temperature or at elevated temperatures, and in solvents such as, but not limited to, those listed above.

It will be appreciated that in order to achieve good yields of the compounds of this invention, it is generally necessary to protect reactive moieties during synthesis. Suitable protecting groups include those listed above, variations thereof, and additional groups known to those skilled in the art. For example, carboxylic acid end-groups may be protected by the formation of alkyl esters, substituted alkyl esters, thio esters, aryl or substituted aryl esters. As is well known to those skilled in the art, the selection of particular protecting groups used in a synthesis depends on a variety of factors, such as reaction conditions and whether or not other protecting groups are used at the same time.

In the compounds of the present invention, $AA_m$ and $AA_p$ preferably designate residues of naturally occurring or synthetic proteinogenic and non-proteinogenic amino acids. Proteinogenic amino acid residues are those amino acids capable of forming proteins, and include Ala, Arg, Asn, Asp, Cys, Glu, Gln, Gly, His, Ile, Leu, Lys, Met, Phe, Pro, Ser, Thr, Tyr, Val, and derivatives thereof. Although these amino acids may exist in either their L— or D— configurations, the L-configuration is preferred. Additionally, non-proteinogenic amino acid residues may be incorporated into branched building units. Although these amino acid residues cannot form proteins on their own, their incorporation into a protein may, for example, aid in determining that protein's active conformers. Reporter groups such as fluorescent amino acids such as 5-hydroxytryptophan, dansyl-lysine, and their derivatives, photolabile amino acid residues, and isotopically labeled amino acids have been used for such purposes. Although these and other non-proteinogenic amino acids may be used in the present invention, $AA_m$ and $AA_p$ are preferably proteinogenic amino acids. $AA_m$ and $AA_p$ can consist of the same or different types of amino acids. The letter m designates an integer of 0 to 10, preferably 0 to 4, and most preferably 0 or 1, while the letter p designates an integer of 1 to 10, preferably 1 to 4, and most preferably 1 or 2.

The branched building units of this invention possess protected or unprotected amide or carboxylic acid groups. These may be represented by X—$AA_m$, $AA_p$—Y, NH—X or COY. X represents an amine or amide hydrogen when a moiety such as the N terminus of the terminal $AA_m$ group or the artificial N terminus formed by U when m=0 is unprotected. Similarly, when a carboxylic acid moiety is unprotected, Y represents the hydroxyl group of the acid. When the amine or amide to which X is attached is protected, X represents a suitable protecting group such as, but not limited to, Boc, Z, Fmoc or Alloc. When a carboxylic acid moiety is protected, Y represents a suitable protecting group such as, but not limited to, alkoxy, substituted alkoxy, allyloxy, substituted allyloxy, aryloxy, and trimethylsilyl ethers; specific examples include OMe, OBzl, OFm, OAll, and $OBu^t$. These protecting groups may be covalently attached to an insoluble polymeric support.

The moiety represented by U in Formula (I) refers to either $C^\alpha ON[(CH_2)_{n+1}W]$ or $\Psi(C^\alpha H_2 N)[CO(CH_2)_q W]$, wherein W is NH—X or COY. $C^\alpha$ represents a carbon atom, and the α carbon of $AA_m$ if m>0, with respect to N; $\Psi(C^\alpha H_2 N)$ represents a reduced carbon-nitrogen bond, and a reduced peptide bond between adjacent $AA_m$ and $AA_p$ residues if m>0. The letter n designates an integer from 1 to 6, preferably an integer from 1 to 4 and the letter q also designates an integer from 1 to 6, preferably an integer from 1 to 4.

The building units of Formula (II) are preferably branched dipeptides. Although these dipeptides may be synthesized by any means known to those skilled in the art, they are preferably synthesized by an approach wherein an amino acid ester is reductively alkylated to yield a N-aminoalkyl- or N-carboxyalkyl amino acid, which is subsequently coupled with a halogenated amino acid. A preferred embodiment of such an approach is shown in Scheme (II):

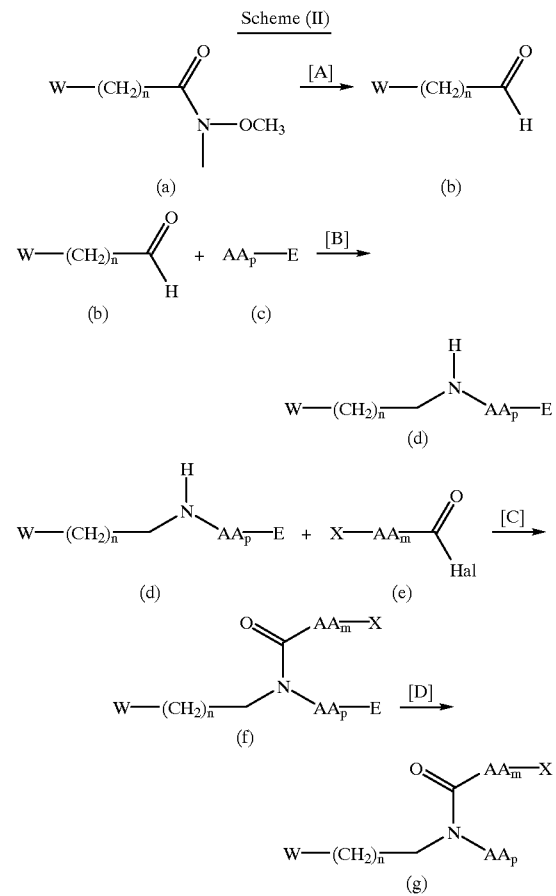

This approach reflects the inventors' discovery that benzyl and tertiary butyl protecting groups can form hydrophobic clusters that restrict the variety of solvents and reactants that may be used to form the building blocks of the present invention.

The reaction conditions represented in Scheme (II) by [A], [B], [C] and [D] may be altered or changed in ways understood by those skilled in the art, and will vary depending upon the particular reactants used and whether the reactions are performed in the liquid or solid phase. Preferably, however, the conditions are as follows: [A] represents reductive conditions suitable for the formation of a compound of Formula (b), and includes the use of, for example, (iso-Bu)$_2$AlH, LiAlH(O—Bu$^t$)$_3$, LiAlH$_4$—EtOH, NaAlH$_4$, and diaminoaluminum hydrides; [B] represents conditions suitable for the reductive alkylation of the compound of Formula (c), and includes the use of catalysts such as H$_2$/Ni, NaCNBH$_3$, and Ag$_2$O for alkylation with BrCH$_2$COOBu$^t$; [C] represents conditions suitable for the coupling of the compounds of Formulas (d) and (e), and includes the use of a coupling agent in the presence of bases such as collidine and DIEA; and [D] represents conditions suitable for the deprotection of the compound of Formula (f), and includes the use of an acid such as acetic acid, hydrochloric acid, and sulfuric acid in the presence of a catalyst such as palladium acetate.

Although the method shown in Scheme (II) is a preferred method of forming building blocks of Formula (I), it is to be understood that variations of this method are encompassed within the present invention. For example, the intermediate of Formula (d) may be deprotected prior its coupling with the compound of Formula (e).

As shown in Scheme (II), an amino acid ester of Formula (c), which is preferably a trimethyl silyl or tertiary butyl ester of an N-alkyl amino acid, is reductively alkylated with an aldehyde of Formula (b):

Formula (b)

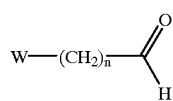

wherein W represents a protected end-group, preferably a protected amide or carboxylic acid, and the protecting moiety is preferably Alloc or OAll. The aldehyde of Formula (b) is preferably, but not necessarily, obtained via the reduction of an N-alkoxyamide. A preferred N-alkoxyamide is the N-methoxyamide of Formula (a):

Formula (a)

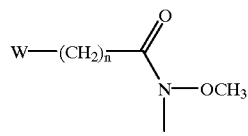

Reaction conditions [A] suitable for such a reduction are known to those skilled in the art, and include the use of reductants such as (iso-Bu)$_2$AlH, LiAlH(O—Bu$^t$)$_3$, LiAlH$_4$—EtOH, NaAlH$_4$, and diaminoaluminum hydrides, although LiAlH$_4$ is preferred. After much investigation, the present inventors have learned that the Alloc and OAll protecting groups are not readily reduced under such conditions, nor are they readily reduced during the following reductive alkylation reaction.

Next, according to Scheme (II), the aldehyde of Formula (b) is reacted with a protected amino acid or peptide ester of Formula (c):

Formula (c)

wherein E represents a carboxyl protecting group such as alkoxy, substituted alkoxy, allyloxy, substituted allyloxy, aryloxy, or trimethylsilyl ether, any of which may be covalently attached to an insoluble polymeric support. Preferred protecting groups include OMe, OBzl, OFm, OAll, and OBu$^t$. This reaction is run under reaction conditions [B] that enable the formation of a compound of Formula (d):

Formula (d)

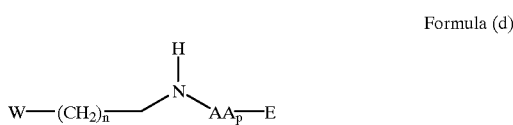

The reaction is preferably run in one of the above disclosed solvents, although DMF is most preferred, and a catalyst is used. Suitable catalysts are known to those skilled in the art and include, for example H$_2$/Ni, NaCNBH$_3$, and Ag$_2$O in the case of BrCH$_2$COOBu$^t$. Preferably, the catalyst is NaCNBH$_3$. After the catalyst is added, the solution is stirred until the reaction is complete; a duration of 24 hours at room temperature is typically sufficient. The protected N-alkylene amino acid product of Formula (d) is then isolated from the reaction mixture using conventional extraction techniques.

The N-alkylene amino acid product of Formula (d) is then coupled with a protected amino acid halide of Formula (e):

Formula (e)

If Halides is Cl, it is preferred that the reaction conditions represented by [C] in Scheme (II) include the use of DCM as the solvent, and a base such as one of those disclosed above. It is preferred, however, that the reaction is performed in the presence of BTSA. If this combination is used, it is further preferred that BTSA is added to a solution of the N-alkylene amino acid Formula (d) at about room temperature over the course of about 24 hours. The solution is preferably then cooled to about 0° C., at which point DIEA is added. At this time, the protected amino acid chloride of Formula (e) is added to the solution while the solution is stirred vigorously. Preferably, the protected amino acid chloride is added to the solution in five equal portions. Stirring is continued at about 0° C. for about 1 hour, and continues after the solution temperature is raised to about room temperature for about another 24 hours or at least until some of the dipeptide building units having Formula (f) are formed. The branched dipeptide building unit may then deprotected prior to isolation and purification, simply isolated and purified, or isolated and purified and then deprotected to yield building blocks of the present invention. It should be noted that Formula (II) encompass both protected compounds of Formula (f) and deprotected compounds of Formula (g).

As indicated by Scheme (II), the compound of Formula (e) need not be a protected amino acid chloride. Indeed, the present inventors have learned that the N-terminal amino acid of the protected dipeptide of Formula (f) can be racemized when the reactant of Formula (e) is an acid chloride. The present inventors have also found, however, that this problem may be avoided if the compound of Formula (e) is a protected amino acid fluoride (i.e., Halides=F). Specifically, it has been discovered that dipeptides of Formula (f) may be obtained in good yield and with a minimum of racemization from the reaction of a Fmoc-AA-fluoride with an N-alkyl amino acid tertiary butyl ester. Without being limited by theory, this is believed to result from the enhanced stabilities of carboxylic acid fluorides as compared to their corresponding chlorides. Furthermore, because the N-alkyl amino acid ester of Formula (c) is more nucleophilic than the free carboxylic group, the fluoride compounds are activated to an extent sufficient to provide good coupling rates. Because different carboxylic acid halides react differently, the reaction conditions represented by [C] in Scheme (II) are preferably different than those described above for Halides=Cl.

The coupling reaction yields a protected dipeptide building block of Formula (f) which may be deprotected by conventional means. Specifically, reaction conditions represented by [D] in Scheme (II) include those that hydrolyze esters. For example, an organic acid such as acetic acid or a mineral acid such as hydrochloric acid and sulfuric acid may be used in the presence of a catalyst such as palladium acetate to remove the protecting group Y.

As described above, the building blocks of Formula (II) are preferably synthesized from N-aminoalkyl or N-carboxyalkyl amino acids of Formula (d):

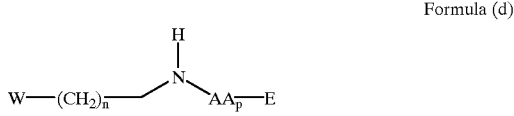

Formula (d)

wherein W is HNX or COY. N-carboxymethyl amino acids may thus be used in the synthesis of the building units of this invention, although N-carboxymethyl amino acids tend to form dioxopiperazines under reaction conditions designated by [C] in Scheme (II). The present inventors have unexpectedly found, however, that the simple extension of the alkyl chain from methyl to ethyl avoids this problem. Accordingly, when Formula (d) represents a N-carboxyalkyl amino acid, it is preferred that it not be a N-carboxymethyl amino acid. It is more preferred that it be a N-carboxyethyl amino acid, which may be synthesized by means other than those shown in Scheme (II). A method of preparing N-aminoalkyl amino acids of Formula (d) that has been found particularly useful in the present invention utilizes Formyl-Meldrum's acid as shown in Scheme (III):

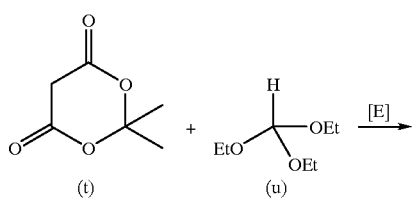

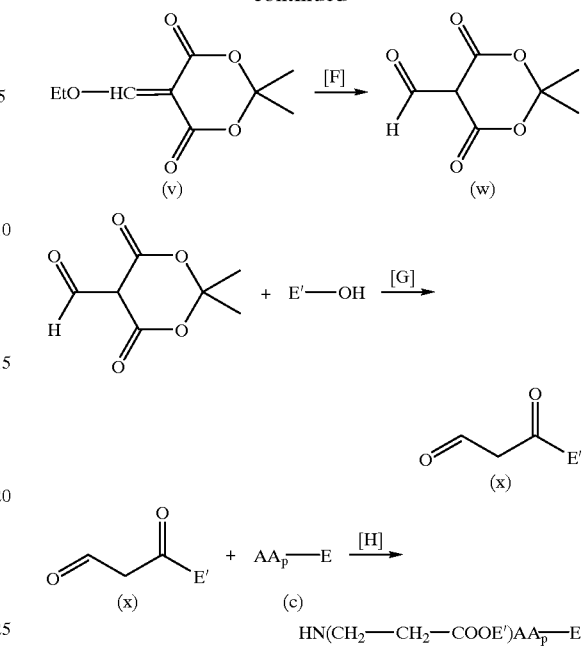

wherein E and E' are carboxyl protecting groups. Suitable carboxyl protecting groups include, but are not limited to, alkoxy, substituted alkoxy, allyloxy, substituted allyloxy, aryloxy, and trimethylsilyl ethers; specific examples include OMe, OBzl, OFm, OAll, and OBu$^t$.

The reaction conditions represented in Scheme (III) by [E], [F], [G] and [H] may be altered or changed in ways understood by those skilled in the art, and will vary depending upon the particular reactants used and whether the reactions are performed in the liquid or solid phase. Preferably, however, the conditions are as follows: [E] represents suitable conditions for coupling compounds of Formulas (t) and (u) for the formation of a compound of Formula (v), and includes conducting the reaction at 90° C. for 3 hours; [F] represents conditions suitable for the rearrangement of the compound of Formula (v) to form the compound of Formula (w), and includes the use of (i) 2 N HCl, room temperature, 30 minutes, and (ii) NaCl; [G] represents conditions suitable for the synthesis of the compound of Formula (x), and includes dry toluene, at reflux, for 1.5 hours; and [H] represents conditions suitable for the coupling of the compounds of Formulas (x) and (c), and includes the use of (i) methanol, 0° C., for 1 hour, and (ii) NaCNBH$_3$.

In another embodiment, the present invention encompasses peptide building units of Formula (III):

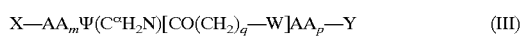

These compounds differ from those of Formula (II) in that they contain a reduced peptide bond between adjacent AA$_m$ and AA$_p$ residues when m>0, and an amide bond to the branching moiety. The reduced peptide bond is indicated by Ψ(C$^\alpha$H$_2$N). Building units of Formula (III) allow more combinations of different protecting groups than those of Formula (II), yet exhibit similar stability in acidic and basic environments.

Although building units of Formula (III) may be synthesized by any means known to those skilled in the art, it is preferred that they be synthesized according to the method shown in Scheme (IV). Advantages of this method include high yields and limited formation of undesirable side-products such as dioxopiperazines.

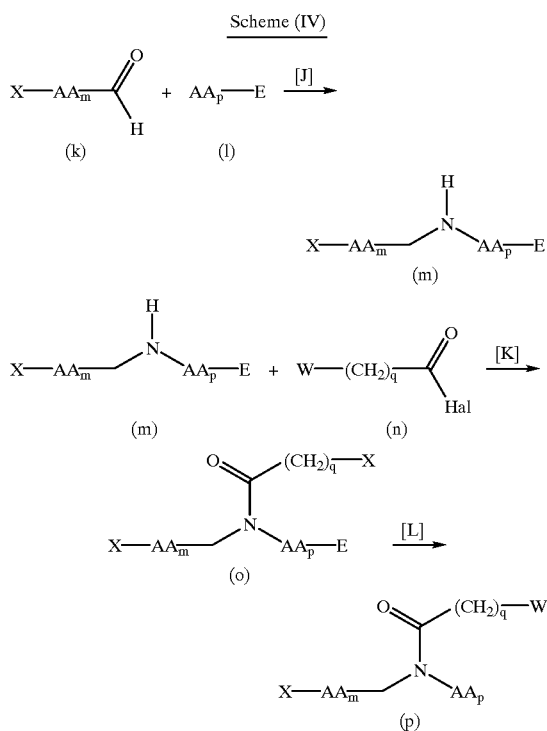

The approach shown in Scheme (IV) is based on an understanding of how aldehyde derivatives of natural and synthetic amino acids may be used to form dipeptides comprising reduced peptide bonds. This approach, like that shown for the first embodiment of the invention, is also based upon the inventors' discovery of novel ways by which aldehydes may be synthesized from protected amino acids, and from Fmoc-protected amino acids in particular. The synthesis of compounds of Formula (k) is thus preferably the same as that of Formula (b) shown in Scheme (II).

The reaction conditions represented in part by [J], [K] and [L] may be altered or changed in ways understood by those skilled in the art, and will vary depending upon the particular reactants used and whether the reactions are performed in the liquid or solid phase. Preferably, however, the conditions are as follows: [J] represents reductive conditions suitable for the formation of a compound of Formula (m), and includes the use of, for example, catalysts such as $H_2/Ni$, $NaCNBH_3$, and $Ag_2O$ in the case of $BrCH_2COOBu^t$; [K] represents conditions suitable for the coupling of the compounds of Formulas (m) and (n), and includes the use of a coupling agent in combination with a base such as collidine and DIEA; and [L] represents conditions suitable for the deprotection of the compound of Formula (o), and includes the use of an acid such as acetic acid, hydrochloric acid, or sulfuric acid in the presence of a catalyst such as palladium acetate.

According to Scheme (IV), an amino acid aldehyde of Formula (k) is coupled with a protected amino acid of Formula (l) to yield a pseudopeptide of Formula (m):

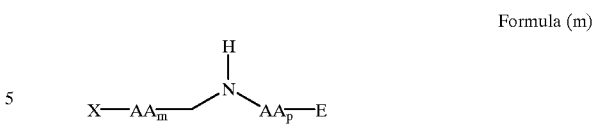

Formula (m)

wherein E is a carboxyl protecting group. Suitable carboxyl protecting groups include, but are not limited to, alkoxy, substituted alkoxy, allyloxy, substituted allyloxy, aryloxy, and trimethylsilyl ethers; specific examples include OMe, OBzl, OFm, OAll, and $OBu^t$. Preferably, the reaction conditions represented by [J] include the use of a catalyst such as $H_2/Ni$, $NaCNBH_3$, or $Ag_2O$ in the case of $BrCH_2COOBu^t$, although other catalysts may of course be used. It has been found that the reaction proceeds smoothly if the solvents are methanol and DMF, respectively.

The compound of Formula (m) is then coupled with a carboxylic acid derivative of Formula (n):

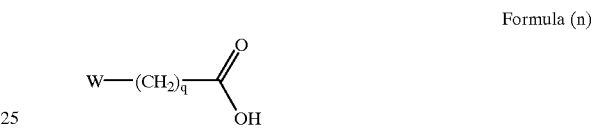

Formula (n)

under reaction conditions represented by [K] in Scheme (IV). Preferably, this reaction is done in DMF with the aid of a coupling agent added after the reactant mixture has been cooled to about 0° C. Suitable coupling agents which may then be added include, for example, HBTU/ HOBT, HATU/ HOBT, or alkyl chloroformates in combination with collidine and DIEA. After all the reactants have been combined, the resulting solution is preferably stirred for about one hour at 0° C. and then overnight at room temperature or at least until branched peptides of Formula (o) are formed. Because the product of this above reaction is crude, it is preferred that the reaction products are recoupled with another coupling agent, preferably PyBrOP®.

The reaction product may be extracted from the solution using, for example, crystallization, precipitation, or flash chromatographic means. If desired, the reaction product is then dissolved in acid, preferably acetic acid, along with a hydrolyzation catalyst such as palladium acetate to form deprotected branched dipeptides of Formula (p).

The building units of Formula (I), which encompasses those of Formulas (II) and (p), may be used in conventional solid phase peptide synthesis, and thus may be bound to other amino acids of an overall peptide structure. The coupling rates of these reactions may be monitored using quantitative tests for free amine groups and by the removal of UV detectable amino protecting groups.

EXAMPLES

The invention is further defined by reference to the following nonlimiting examples. The compounds described in these examples were analyzed using a variety of techniques including thin layer chromatography (TLC), high pressure liquid chromatography (HPLC), and fast atomic bombardment mass spectroscopy (FAB-MS). Thin layer chromatography was conducted using silica gel 60, F254, Merck 0.25 mm glass plates using the following solvent systems: $S_1$=hexane-ethyl acetate 1/1 v/v; $S_2$=chloroform-methanol 7/3 v/v; $S_3$=chloroform-methanol 9/1 v/v; $S_4$=chloroform-methanol-acetic acid 90/8/2 v/v/v; $S_5$=n-butanol-acetic acid-water 4/1/1 v/v/v; $S_6$=benzene-acetoneacetic acid 27/10/0.5 v/v/v. HPLC measurements utilized a Knauer Column (220 nm, HD-SIL-18-5s-80A, 250×4 mm) with a gradient that began from 20% acetonitrile in 0.1% aqueous TFA and progressed to 80% acetonitrile at a rate of 1% /min; a flow rate of 1.0 ml/min was used. These examples are representative, and should not be construed to limit the scope of the present invention.

Example 1

H—Phe—OMe•HCl (2.16 g/ 10 mmol) was dissolved in 50 ml freshly distilled DMF. Tertiary butyl bromoacetate (2.44 g/ 12.5 mmol) and silver(I)oxide (5.79 g/ 25 mmol) were added under stirring at room temperature. Stirring was continued for 24 hours during which the color of the silver oxide changed from black to grey. The reaction process was monitored by TLC (system 1/ ninhydrine): the starting material H—Phe—OMe•HCl disappeared as a new, main spot was detected. After reaction completion, the mixture was filtered through a silica gel bed to remove the silver salts. The precipitate was washed with DMF (3×10 ml) and the filtrates were evaporated to dryness under vacuum. The residue was dissolved in ethyl acetate (50 ml) and extracted with 5% $KHSO_4$ (3×10 ml), 10% $NaHCO_3$ (3×10 ml) and saturated aqueous NaCl. After drying with anhydrous $Na_2SO_4$ the solvent was removed under vacuum. The resulting oil (2.12 g/ 72% yield) was pure by TLC and HPLC. No H—Phe—OMe•HCl was detected (HPLC $t_R$ 5.10 min) and no diketopiperazine formation was observed. After acetylation with $Ac_2O$/ DIEA and saponification by LiOH/ THF at 25C °, the spot (TLC) of the product disappears within 90 minutes.

| Yield: | 2.12 g (72%) | |
| --- | --- | --- |
| | $C_{16}H_{23}NO_4$ | M.W. = 293.3 |
| | $[\alpha]_D$ = n.d. | |
| TLC Results: | $R_f$:(S1) | 0.68 (benzene:acetone:acetic acid 27:10:0.5) |
| | $R_f$:(S2) | 0.82 (chloroform:methanol/ 9:1) |
| | $R_f$:(S3) | 0.56 (hexane:ethyl acetate/ 1:1) |
| HPLC Results: | $t_R$ 17.54 min | |
| EI-MS: | m/e[MH$^+$] | 294.3 |

Example 2

Fmoc—D—Phe-Ψ[CO—N($CH_2$COOBu$^t$)]Phe—OH

A mixture of HN($CH_2$COOBu$^t$)Phe—OH (0.279 g, 1.0 mmol) in DCM (10 ml) was treated with BTSA (0.98 ml, 4 mmol) at room temperature for 24 hours. The clear solution was cooled to 0° C. and DIEA (0.21 ml, 1.25 mmol) was added. The reaction mixture was stirred vigorously and Fmoc—D—Phe—Cl (0.507 g, 125 mmol) was added in five portions. Carpino, L. A. et al., J. Org. Chem. 51:3732–3734 (1986). Stirring was continued for 1 hour at 0° C. and then 24 hours at room temperature. The solvent was removed and the residue taken up with ethyl acetate (30 ml), washed with 0.1 N $KHSO_4$ (3×10 ml), saturated with aqueous NaCl solution (3×10 ml), dried over $Na_2SO_4$; and evaporated to dryness. The residue was purified by flash chromatography on silica gel 60 (chloroform/methanol 94/6). Still W. C. et al. J. Org. Chem. 14:2923–2925 (1978). The fractions containing pure products were combined, evaporated and dried under vacuum.

| Yield: | 0.305 g (0.47 mmol) | 47.0% |
| --- | --- | --- |
| | $C_{39}H_{40}N_2O_4$ | M.W. = 648.73 g/mol |
| | $[\alpha]_D$: | −10.9°(c = 1.0 MeOH) |
| TLC Results: | $R_f$:(S3) | 0.46 |
| | $R_f$:(S4) | 0.86 |
| HPLC Results: | $t_R$: | 50.6 min |
| FAB-MS: | 631 ((M − $H_2O$)$^+$), 650 ((M + 1)$^+$) | |

Example 3

Fmoc—D—Phe-Ψ[CO—N($CH_2CH_2$NHBoc)]Phe—OH

A suspension of HN($CH_2CH_2$NHBoc)Phe—OH (0.308 g, 1.0 mmol) in DCM (10 ml) was treated with BTSA (0.98 ml, 4 mmol) at room temperature for 24 hours. The clear solution was cooled to 0° C. and DIEA (0.22 ml, 1.25 mmol) was added. The reaction mixture was stirred vigorously and Fmoc—D—Phe—Cl (0.507g, 1.25mmol) was added in five portions within 20 minutes. Carpino et al. J. Org. Chem. 51:3732–3734 (1986). Stirring was continued for 1 hour at 0° C. and then 24 hours at room temperature. The solvent was removed and the residue taken up with ethyl acetate (30 ml), washed with 0.1 N $KHSO_4$ (3×10 ml), saturated aqueous NaCl solution (3×10 ml), dried over $Na_2SO_4$; and evaporated to dryness. The residue was purified by flash chromatography on silica gel 60 (chloroform/methanol 92/8). Still et al. J. Org. Chem. 14:2923–2925 (1978). The fractions containing pure product were combined, evaporated and dried under vacuum to yield a pale yellow oil.

| Yield: | 0.293 g (0.43 mmol) 43.3% | |
| --- | --- | --- |
| | $C_{40}H_{43}N_3O_7$ | M.W. = 677.77 g/mol |
| | $[\alpha]_D$: | −21.4°(c = 1.0 MeOH) |
| TLC Results: | $R_f$:(S3): | 0.45 |
| | $R_f$:(S4): | 0.52 |
| HPLC Results: | $t_R$: | 48.4 min |
| FAB-MS: | 578 ((M + 1 − Boc)$^+$), 678 (M$^+$), 716 ((M − 1 + K)$^+$) | |

Example 4

Fmoc—ValΨ[CO—N($CH_2$COOBu$^t$)]Phe—OH

A mixture of HN($CH_2$COOBu$^t$)Phe—OH (2.0 g, 7.16 mmol) in DCM (100 ml) was treated with BTSA (7.00 ml, 28.64 mmol) at room temperature for 24 hours. The clear solution was cooled to 0° C. and DIEA (1.425 ml, 8.59 mmol) was added. The reaction mixture was stirred and Fmoc—Val—Cl (2.55 g, 7.16 mmol) was added in five portions. Stirring was continued for 1 hour at 0° C. and then for 24 hours at room temperature. The solvent was removed and the residue taken up with ethyl acetate (100 ml), washed with 0.1 M $KHSO_4$ (3×30 ml), saturated aqueous NaCl solution (3×30 ml), dried over $Na_2SO_4$; and evaporated to dryness. The residue was purified by flash chromatography on silica gel 60( chloroform/methanol 94/6). The fractions containing pure product were combined, evaporated and dried under vacuum.

| Yield: | 1.67 g (39%) | (purified) |
| --- | --- | --- |
| | $C_{35}H_{40}N_2O_7$ | M.W. 600.69 |

|  |  |  |
|---|---|---|
|  | $[\alpha]_D$ | -34.5°(c = 1.0, MeOH) |
| TLC Results: | $R_f$:(S$_3$) | 0.68 |
|  | $R_f$:(S$_4$) | 0.71 |
| HPLC Results: | $t_R$: | 51.2 min |
| FAB-MS: | 601 (M + 1)$^+$ |  |

Example 5

Fmoc—ValΨ[CO—N(CH$_2$—CH$_2$—CH$_2$—NHBoc)]Phe—OH

A suspension of HN(CH$_2$—CH$_2$—CH$_2$—NHBoc)]Phe—OH (322 mg, 1.0 mmol) in DCM (20 ml) was treated with N,O-bis(trimethylsilyl)acetamide (980 μl, 4.0 mmol) at room temperature for 20 hours. The clear solution was cooled to 0° C. and DIEA (340 μl, 2.0 mmol) was added. The reaction mixture was stirred and Fmoc—Val—Cl (446 mg, 1.25 mmol) added over the course of 20 minutes. Stirring was continued for 1 hour at 0° C. and then for 24 hours at room temperature. The solvent was removed and the residue taken up in ethyl acetate (100 ml), washed with 0.1 M KHSO$_4$ (3×30 ml), saturated aqueous NaCl solution (3×30 ml), dried over Na$_2$SO$_4$; and evaporated to dryness. The crude product were purified by flash chromatography on silica gel 60 (chloroform/methanol 91/9). The fractions containing pure product were combined, evaporated and dried under vacuum to yield a pale yellow oil.

|  |  |  |
|---|---|---|
| Yield: | 0.277 g (43%) | (purified) |
|  | C$_{37}$H$_{45}$N$_3$O$_7$ | M.W. 643.79 |
|  | $[\alpha]_D$ | -40.3°(c = 1.0, MeOH) |
| TLC Results: | $R_f$:(S$_2$) | 0.63 |
|  | $R_f$:(S$_3$) | 0.65 |
| HPLC Results: | $t_R$: | 48.50 min |
| FAB-MS: | 644 (M$^+$) |  |

Example 6

Fmoc—ValΨ[CO—N(CH$_2$—CH$_2$—NHBoc)]Phe—OH

A suspension of HN(CH$_2$—CH$_2$—NHBoc)]Phe—OH (925 mg, 3.0 mmol) in DCM (20 ml) was treated with N,O-bis(trimethylsilyl)acetamide (2.94 ml, 12 mmol) at room temperature for 20 h. The clear solution was cooled to 0° C. and DIEA (0.64 ml, 3.75 mmol) was added. The reaction mixture was stirred and Fmoc—Val—Cl (1.34 g, 3.75 mmol) added in some portions within 20 min. Stirring was continued for 1 hour at 0° C. and 24 hours at room temperature. The solvent was removed and the residue taken up in ethyl acetate (100 ml), washed with 0.1 M KHSO$_4$ (3×30 ml), saturated aqueous NaCl solution (3×30 ml), dried over Na$_2$SO$_4$; and evaporated to dryness. The crude product were purified by flash chromatography on silica gel 60 (chloroform/methanol 91/9). The fractions containing pure product were combined, evaporated and dried under vacuum to yield a pale yellow oil.

|  |  |  |
|---|---|---|
| Yield: | 0.756 g (40%) | (purified) |
|  | C$_{36}$H$_{43}$N$_3$O$_7$ | M.W. 629.76 |
|  | $[\alpha]_D$: | -10.7°(c = 1.0, MeOH) |

|  |  |  |
|---|---|---|
| TLC Results: | $R_f$:(S$_2$) | 0.72 |
|  | $R_f$:(S$_3$) | 0.65 |
| HPLC Results: | $t_R$: | 48.36 min |
| FAB-MS: | 630 (M$^+$) |  |

Example 7

Boc—β—Ala Ψ[CH$_2$NH]Phe—OBzl

Boc—βAla Ψ(CH$_2$—NH)Phe—OBzl (5.0 g, 12.12 mmol) was hydrogenated in aqueous acetic acid (90%, 50 ml) with Pd-acetate (250–500 mg) for 12 hours. The reaction was monitored by TLC in hexane-ethylacetate 1/1. The catalyst was filtered off and the residue was washed with 90% acetic acid. The filtrates were evaporated in vacuo, the residue washed with benzene and concentrated in vacuo. The remaining product was finally treated with diethyl ether to yield a white solid substance.

|  |  |  |
|---|---|---|
| Yield: | 2.5 g (64%) |  |
|  | C$_{17}$H$_{26}$N$_2$O$_4$ | M.W. 322.4 |
| TLC Results: | $R_f$:(S$_1$) | 0 |
|  | $R_f$:(S$_4$) | 0.28 |
|  | $R_f$:(S$_5$) | 0.64 |
| HPLC Results: | $t_R$ | 14.01 (min) |
| FAB-MS: | 323 (M + 1)$^+$ |  |

Example 8

Fmoc—Val Ψ[CH$_2$N(CO—CH$_2$—CH$_2$—NHBoc)]Phe—OBzl and Z—ValΨ[CH$_2$—N(CO—CH$_2$—CH$_2$—NHBoc)Phe—OBzl Z—ValΨ[CH$_2$NH]Phe—OBzl (2.5 g, 4.9 mmol) were dissolved in 20 ml of DMF, cooled to 0° C., and added consecutively with Boc—βAla (1.85 g, 9.8 mmol), HATU (3.72 g, 9.8 mmol), HOBt (1.33 g, 9.8 mmol) and DIEA (3.24 ml, 19.6 mmol). The reaction solution was stirred 1 hour at 0° C. and overnight at room temperature. The solvent was removed under vacuum and the residue dissolved in 200 ml ethylacetate to provide a solution which was then washed with 0.1 M KHSO$_4$, with 0.1 M NaHCO$_3$ and with water. After drying over Na$_2$SO$_4$, the ethylacetate was removed.

The resulting solid residue (3 g) contained both pseudo-dipeptide and Boc—βAla, and so the crude product was recoupled with PyBrop. The reaction product was resolved in 120 ml CH$_2$Cl$_2$ and added to Boc—βAla (1.85 g), PyBrop (4.56 g, 9.8 mmol), and DIEA (4.86 ml, 29.6 mmol) at 0° C. The reaction mixture was stirred for 72 hours at room temperature. After the solvent was removed, the residue was dissolved in 200 ml ethylacetate and again extracted as described above. After the ethylacetate was removed, the crude reaction product was dissolved in 60 ml methanol and precipitated with 0.6% aqueous acetic acid. The precipitate shows a purity sufficient for further use in the following steps.

|  |  |  |
|---|---|---|
| Yield: | 71% |  |
|  | C$_{37}$H$_{47}$N$_3$O$_7$ | M.W. 645.77 |
|  | F.183–185° C. |  |

|  |  |  |
|---|---|---|
|  | $[\alpha]^{20} = -2.7 \pm 1$ | (c = 1.0, CH$_3$OH) |
|  | E$_A$(Arg) = 0 |  |
| TLC Results: | R$_f$: | 0.6 (hexane/ethyl acetate 8:2) |
|  | R$_f$:(S$_6$) | 0.64 |
| HPLC Results: | t$_R$: | 51.04 min |
| FAB-MS: | [M$^+$]: obsd. 646 |  |

Example 9

H—ValΨ[CH$_2$—N(CO—CH$_2$—CH$_2$—NHBoc)]Phe—OH

Z—ValΨ[CH$_2$—N(CO—CH$_2$—CH$_2$—NHBoc)]Phe—OBzl (0.5 g) was dissolved in 50 ml acetic acid (95%) and hydrogenated in the presence of catalyst (palladium acetate). The catalyst was added in three portions. After hydrogenation overnight the catalyst was removed by filtration and the solution was evaporated to dryness. The triturated crude product was extracted with ethyl ether, dissolved in n-butanol and washed with 0.1 M KHSO$_4$. The butanol solution was washed with water and evaporated.

| Yield: | 30–45% |  |
|---|---|---|
|  | C$_{22}$H$_{35}$N$_3$O$_5$ | M.W. 421.51 |
|  | F. degradation |  |
|  | [α] = +12.9 ± 1 (c = 1.0, CH$_3$OH) |  |
|  | E$_A$(Arg) = 0 |  |
| TLC Results: | R$_f$:(S$_2$) | 0.6 |
|  | R$_f$:(S$_4$) | 0.2 |
|  | R$_f$:(S$_5$) | 0.55 |
|  | R$_f$:(S$_6$) | 0.3 |
| HPLC Results: | t$_R$: | 23.4 min |
| FAB-MS: | [M$^+$]: obsd. 422 |  |

Example 10

HN(CH$_2$—CH$_2$—COOAll)Phe—OBu$^t$

A solution of formyl Meldrum's acid (6.0 g, 34.8 mmol) and allylic alcohol (2.85 ml, 41.8 mmol) in dry toluene (60 ml) was refluxed for 1.5 hours. The solvent was evaporated under vacuum and the crude product used without further purification.

The crude product was dissolved in absolute methanol (30 ml) and added to a solution of H—Phe—OBu$^t$·HAc (9.79 g, 34.8 mmol) and triethylamine (5.4 ml, 34.8 mmol) in dry methanol (30 ml) at 0° C. The solution was stirred with 3 g molecular sieves at room temperature for 1 hour, and then NaCNBH$_3$ (2.4 g, 38.3 mmol) was added at 0° C. Stirring continued at room temperature for 12 hours. The reaction mixture was then filtered and the solvent was removed. The residue was taken up with ethyl acetate (200 ml), washed with 5% KHSO$_4$ (6×600 ml), 5% NaHCO$_3$ (3×100 ml), saturated aqueous NaCl solution (3×100 ml), dried over Na$_2$SO$_4$; and evaporated to dryness to yield a white powder.

| Yield: | 61% |  |
|---|---|---|
|  | C$_{19}$H$_{27}$NO$_4$ | MW: 333.42 |
| TLC Results: | R$_f$: | 0.82 (hexane/ethyl acetate 1/1 v/v) |
| HPLC Results: | t$_R$: | 27.7 min |
| FAB-MS: | 334 (M + H) |  |

Example 11

HN(CH$_2$—CH$_2$—CH$_2$—NH-Alloc)Phe—OBu$^t$ 18.0 g (83.24 mmol) Alloc-βAla—N,O-dimethylhydroxamate was dissolved in 200 ml dry ether and cooled to 0° C. To the clear solution 3.9 g (103.9 mmol) LiAlH$_3$ was added carefully in small portions. The reaction mixture was stirred for 10 minutes at 0° C. and 40 minutes at room temperature. The reaction was finished with KHSO$_4$ (19.8 g, 145.7 mmol) in 100 ml water at 0° C. The ether phase was separated and the suspension of LiAlH$_3$/KHSO$_4$ was washed 3 times with ether (50 ml). The ether phase was extracted with KHSO$_4$ (3×30 ml), NaHCO$_3$ (3×50 ml) and NaCl (3×50 ml). The aldehyde (oil) was used as crude product. Yield: 8.0 g Phe—OBu$^t$·HAc (14.3 g, 50.8 mmol) was dissolved in dry methanol (50 ml) cooled to 0° C., triethylamine (7.0 ml, 50.8 mmol) and Alloc-βAla—CHO (8.0 g, 50.8 mmol) in 50 ml methanol and molecular sieve (2–3 g) were added. The reaction mixture was stirred for 1 hour at room temperature, cooled to 0° C. and then NaCNBH$_3$ (3.52 g, 55.9 mmol) was added in small portions. The stirring was continued for 12 hours at room temperature. After removing the molecular sieves, the solvent was evaporated, the residue was taken up with ethyl acetate (150 ml), washed with KHSO$_4$ 3×30 ml), NaHCO$_3$ (3×50 ml) and NaCl (3×50 ml). The organic phase was dried over Na$_2$SO$_4$ and the solvent removed by evaporation. The crude product (17 g) was washed with ether and hexane to get a white powder.

| Yield: | 42% |  |
|---|---|---|
|  | C$_{20}$H$_{30}$N$_2$O$_4$ | MW: 362.46 |
| TLC Results: | R$_f$: | 0.44 (hexane/ethyl acetate 1/1 v/v) |
|  |  | 0.58 (chloroform/methanol 9/1 v/v) |
|  |  | 0.84 (n-butanol/HAc/water 4/1/1 v/v/v) |
| HPLC Results: | t$_R$: | 27.14 min |
| FAB-MS: | 363 (M + H) |  |

Example 12

Fmoc—DPheΨ[CO—N(CH$_2$—CH$_2$—CH$_2$—NHAlloc)]Phe—OH

To a solution of NH(CH$_2$—CH$_2$—CH$_2$—NHAlloc)Phe—OBu$^t$ (0.8 g, 2.2 mmol) in dry DCM were mixed 440 μl collidine (3.3 mmol) and 1.8 g Fmoc—DPhe—F (4.4 mmol). The clear solution was stirred by 50° C. over 4 hours. The solvent was removed under vacuum and the crude product was resolved in ethyl acetate and extracted with 5% KHSO$_4$ (3×30 ml), NaHCO$_3$ (3×30 ml) and NaCl (3×30 ml). The dry organic layer was evaporated under vacuum.

Fmoc—DPheΨ[CO—N(CH$_2$—CH$_2$—CH$_2$—NHAlloc)]Phe—OBu$^t$ was purified by flash chromatography on silica gel 60 (MERCK) with pure chloroform. The fractions without Fmoc—DPhe—OH were collected and evaporated under vacuum. The resulting oil was treated with 50% TFA/DCM (and some drops of water) for 2 hours at room temperature. The product (1.0 g) was obtained as an oil and purified by flash chromatography on silica gel with chloroform/methanol 94/6.

| Yield: | 44% |  |
|---|---|---|
|  | C$_{40}$H$_{41}$N$_3$O$_7$ | MW: 675.75 |
|  | [α]$_D$ | −26.3°(c = 1.0, MeOH) |
| TLC Results: | R$_f$: | 0.42 (chloroform/methanol 9/1 v/v) |
|  | R$_f$(S3) | 0.5 |
| HPLC Results: | t$_R$ | 47.34 min |
| FAB-FAB-MS: | 676 (M$^+$) |  |

Example 13

Fmoc—ValΨ[CO—N(CH$_2$—CH$_2$—COOAll)]Phe—OH

To a mixed solution of NH(CH$_2$—CH$_2$—COOAll)Phe—OBu$^t$ (700 mg, 2.1 mmol) in DCM, 417 μl collidine (3.15 mmol) and 1.5 g Fmoc—Val—F (4.12 mmol) were added. The clear solution was stirred at 50° C. bath temperature for 4 hours. The reaction mixture was extracted with $KHSO_4$ (3×30 ml), $NaHCO_3$ (3×30 ml) and NaCl (3×30 ml). The dried organic phase was evaporated under vacuum, and the resulting oil was treated with TFA/DCM 1:1 (and some drops of water) for 2 hours at room temperature. The TFA/DCM-solution was evaporated under vacuum and washed 3 times with ether. The crude product was obtained as an oil and purified by flash chromatography on silica gel 60 (MERCK) system 92/8 chloroform/methanol.

| Yield: | 33% | |
| --- | --- | --- |
| | $C_{35}H_{38}N_2O_7$ | MW: 598.67 |
| | $[\alpha]_D^{25}$: | −75 ± 1°(c = 1, MeOH) |
| TLC Results: | $R_f$: | 0.46 (chloroform/methanol 9/1 v/v) |
| HPLC Results: | $t_R$ | 48.35 min |
| FAB-MS: | 599.6 (M + H) | |

Example 14

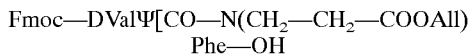
Fmoc—DValΨ[CO—N($CH_2$—$CH_2$—COOAll)Phe—OH

To a mixed solution of NH($CH_2$—$CH_2$—COOAll)Phe—OBu$^t$ (230 mg, 0.7 mmol) in DCM, 139 μl collidine (1.05 mmol) and 510 mg Fmoc—DVal—F (1.4 mmol) were added. The clear solution was stirred at 50° C. bath temperature for 4 hours. The reaction mixture was extracted with $KHSO_4$ (3×30 ml), $NaHCO_3$ (3×30 ml) and NaCl (3×30 ml). The dried organic phase was evaporated under vacuum and the resulting oil was treated with TFA/DCM 1:1 (and some drops of water) for 2 hours at room temperature. The TFA/DCM-solution was evaporated under vacuum and washed 3 times with ether. The crude product was an oil which was purified by flash chromatography on silica gel 60 (MERCK) system 93/7 chloroform/methanol.

| Yield: | 35% | |
| --- | --- | --- |
| | $C_{35}H_{38}N_2O_7$ | MW: 598.67 |
| | $[\alpha]_D^{25}$: | −34 ± 1° (c = 1, MeOH) |
| TLC Results: | $R_f$: | 0.42 (chloroform/methanol 9/1 v/v) |
| | $R_f$: (S3) | 0.55 |
| | $R_f$: (S6) | 0.58 |
| HPLC Results: | $t_R$ | 47.76 min |
| FAB-MS: | 599.9 (M + H) 597,5 (M − H) | |

Example 15

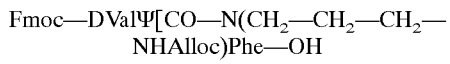
Fmoc—DValΨ[CO—N($CH_2$—$CH_2$—$CH_2$—NHAlloc)Phe—OH

To a mixed solution of NH($CH_2$—$CH_2$—$CH_2$—NHAlloc)Phe—OBu$^t$ (200 mg, 0.56 mmol) in DCM, 100 μl collidine (0.84 mmol) and 400 mg Fmoc—DVal—F (1.12 mmol) were added. The clear solution was stirred at 50° C. bath temperature for 4 hours. The reaction mixture was extracted with $KHSO_4$ (3×30 ml), $NaHCO_3$ (3×30 ml) and NaCl (3×30 ml). The dried organic phase was evaporated under vacuum and the resulting oil was treated with TFA/DCM 1:1 (and some drops of water) for 2 hours at room temperature. The TFA/DCM-solution was evaporated under vacuum and washed 3 times with ether. The crude product was obtained as an oil and was purified by flash chromatography on silica gel 60 (MERCK) system 94/6 chloroform/methanol.

| Yield: | 35% | |
| --- | --- | --- |
| | $C_{36}H_{41}N_3O_7$ | MW: 627.71 |
| | $[\alpha]_D$ | −28.7° (c = 1.0, MeOH) |
| TLC Results: | $R_f$: (S3) | 0.51 |
| | $R_f$: (S6) | 0.48 |
| HPLC Results: | $t_R$ | 45.47 min |
| FAB-MS: | 628.8 (MH)$^+$ | |

Example 16

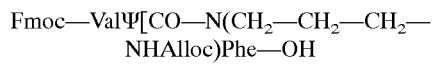
Fmoc—ValΨ[CO—N($CH_2$—$CH_2$—$CH_2$—NHAlloc)Phe—OH

To a mixed solution of NH($CH_2$—$CH_2$—$CH_2$—NHAlloc)Phe—OBu$^t$ (2.1 g, 5.88 mmol) in DCM, 1.19 ml collidine (8.82 mmol) and 4.2 g Fmoc—Val—F (11.8 mmol) were added. The clear solution was stirred at 50° C. bath temperature for 4 hours. The reaction mixture was extracted with $KHSO_4$ (3×30 ml), $NaHCO_3$ (3×30 ml) and NaCl (3×30 ml). The dried organic phase was evaporated under vacuum to yield an oil, which was then treated with TFA/DCM 1:1 (and some drops of water) for 2 hours at room temperature. The TFA/DCM-solution was evaporated under vacuum and washed 3 times with ether. The crude product was obtained as an oil, which was purified by flash chromatography on silica gel 60 (MERCK), system chloroform/methanol 92/8.

| Yield: | 39% | |
| --- | --- | --- |
| | $C_{36}H_{41}N_3O_7$ | MW: 627.71 |
| | $[\alpha]_D$ | −59.7° (c = 1.0, MeOH) |
| TLC Results: | $R_f$: (S3) | 0.56 |
| | $R_f$: (S6) | 0.54 |
| HPLC Results: | $t_R$ | 47.29 min |
| FAB-MS: | 628.6 (M + H) | |

Example 17

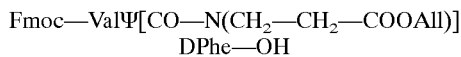
Fmoc—ValΨ[CO—N($CH_2$—$CH_2$—COOAll)]DPhe—OH

To a solution of NH($CH_2$—$CH_2$—COOAll)DPhe —OBu$^t$ (1.0 g, 3.0 mmol) in dry DCM were mixed 597 μl collidine (4.5 mmol) and 2.15 g Fmoc—Val—F (6.0 mmol). The clear solution was stirred at 50° C. for 4 hours. The solvent was then removed under vacuum and the crude product was resolved in ethyl acetate and extracted with solution of 5% $KHSO_4$ (3×30 ml), saturated $NaHCO_3$ (3×30 ml), and saturated NaCl (3×30 ml). The dried ($Na_2SO_4$) organic layer was evaporated under vacuum.

Fmoc—ValΨ[CO—N($CH_2$—$CH_2$—COOAll)]DPhe—OBu$^t$ was purified by flash chromatography on silica gel 60 (MERCK) with pure chloroform. The fractions without Fmoc—Val—OH were collected and evaporated under vacuum. The resulting oil was treated with 50% TFA/DCM (and some drops of water) for 2 hour at room temperature. The crude product (1.0 g) was obtained as an oil, which was purified by flash chromatography on silica gel with chloroform /methanol 96/4.

| | | | |
|---|---|---|---|
| Yield: | 32% | | |
| | $C_{35}H_{38}N_2O_7$ | MW: 598.67 | |
| | $[\alpha]_D^{25}$ | +30.68° ± 1 (c = 1,MeOH) | |
| TLC Results: | $R_f$: (S3) | 0.55 | |
| | $R_f$: (S6) | 0.58 | |
| | HPTLC-plates (Silica gel 60 $F_{254}$, Merck HPTLC-glass plates) | | |
| HPLC Results: | $t_R$: HPLC (Knauer, 220 nm, HD-SIL 18-5s-80, 250 × 4 mm, gradient from 20% acetonitrile containing 0.1% TFA to 80% acetonitrile, flow rate 1 ml/min) | 47.11 min | |
| FAB-FAB-MS: | 599 ($M^{+}$) | | |

Example 18

Synthesis of Fmoc—Val—Hydroxamate

One equivalent of Fmoc—Val—OH (10.00 mmol; 3.4 g) and 1 equivalent N,O-dimethylhydroxylamine hydrochloride (10.00 mmol; 1.08 g) were dissolved in 100 ml of DCM. The mixture as cooled to 0° C., at which point 1.1 equivalent DIEA (11.00 mmol; 1.88 ml) and 1 equivalent N,N'-dicyclohexylcarbodiimid (10.00 mmol; 2.06 g) were added and stirring was continued at 0° C. for 1 hour, and then at room temperature for 4 hours. The precipitating dicyclohexyl urea was filtered off and the solvent was removed under vacuum. The residue was dissolved in ethyl acetate and extracted with $KHSO_4$ (3×), $NaHCO_3$ (3×) and NaCl (3×). After drying with $Na_2SO_4$ and concentrating under vacuum, a wax-like substance was obtained. Remaining dicyclohexyl urea was separated using diethyl ether. The urea was filtered off, and the solvent removed under vacuum.

| | | | |
|---|---|---|---|
| Yield: | 93% | | |
| | $C_{22}H_{26}N_2O_4$ | $M_W$ 382 g/mol | |
| TLC Results: | $R_f$: (S6) | 0.41 | |
| HPLC Results: | $t_R$ | 38.10 | (20–80% B in 60 min; Vydac C18) |
| FAB-MS: | $[MH]^+$ 383 | | |

Example 19

Synthesis of Fmoc—Val—CHO

One equivalent Fmoc—Val—hydroxamate (13.07 mmol; 5.00 g) was dissolved in dry THF. This solution was evacuated and covered with argon. The mixture was then cooled to −15° C. and 1.25 equivalents $LiAlH_4$ (16.33 mmol; 0.62 g) was carefully added in portions. Stirring was continued at −15° C. for 15 min and then at room temperature for 1 hour. The mixture was then hydrolyzed with a concentrated solution of 1.75 equivalents $KHSO_4$ (22.87 mmol; 3.11 g), and the THF was evaporated under vacuum. The remaining aqueous solution was extracted with diethyl ether several times. The extracts were combined and extracted with $KHSO_4$ (3×), $NaHCO_3$ (3×) and NaCl (3×). After drying with $Na_2SO_4$ and concentrating under vacuum, an oil was obtained that was immediately used for further processing.

| | | | |
|---|---|---|---|
| Yield: | 60–80% | | |
| | $C_{20}H_{21}NO_3$ | $M_W$ 323 g/mol | |
| HPLC Results: | $t_R$ | 36.26 | (20–80% B in 60 min; Vydac C18) |
| FAB-MS: | $[MH]^+$ 324 | | |

Example 20

Synthesis of Fmoc—ValΨ[$CH_2NH$]Phe—$OBu^t$

One equivalent Phe—$OBu^t$xHAc (30.95 mmol; 8.72 g) was treated with 1 equivalent triethylamine (30.95 mmol; 4.31 ml) and was then added to a solution of 1 equivalent Fmoc—Val—CHO (30.95 mol; 10.00 g) in dry methanol with molecular sieves. This mixture was stirred for 1 hour before it was cooled to 0° C., at which point 1.1 equivalent $NaCNBH_3$ (34.05 mmol; 2.14 g) was added in portions. Stirring was continued overnight. The molecular sieves were filtered off and the methanol removed under vacuum to provide a residue which was then dissolved in ethyl acetate and extracted with $KHSO_4$ (3×), $NaHCO_3$ (3×) and NaCl (3×). After drying with $Na_2SO_4$ and concentrating under vacuum, a white solid compound was obtained.

| | | | |
|---|---|---|---|
| Yield: | 83% (crude product) | | |
| | $C_{33}H_{40}N_2O_4$ | $M_W$ 528 g/mol | |
| TLC Results: | $R_f$: (S6) | 0.41 | |
| HPLC Results: | $t_R$ | 42.21 | (20–80% B in 60 min Vydac C18) |
| FAB-MS: | $[MH]^+$ 529 | | |

Example 21

Synthesis of Fmoc—ValΨ[$CH_2N$ ($COCH_2CH_2NHAlloc$)]Phe—$OBu^t$

One equivalent Alloc-β-Ala (2 mmol; 0.346 g) was dissolved in dry THF and cooled to −15° C. One equivalent N-methyl morpholine (2 mmol; 0.22 ml) and 1 equivalent isobutyl chloroformate (2 mmol; 0.264 ml) were then added. After 10 minutes, a solution of 1 equivalent Fmoc—ValΨ [$CH_2NH$]Phe—$OBu^t$ (2 mmol; 1.056 g) and 1 equivalent N-methyl morpholine (2 mmol; 0.22 ml) in dry THF was added. The mixture was allowed to warm up gently to room temperature. After stirring overnight, the THF was removed and the residue dissolved in ethyl acetate, extracted with $KHSO_4$ (3×), $NaHCO_3$ (3×) and NaCl (3×). The organic phase was dried with $Na_2SO_4$, and the solvent removed under vacuum to provide a yellow oil.

| | | | |
|---|---|---|---|
| Yield: | 92% (crude product) about 35% content | | |
| | $C_{40}H_{49}N_3O_7$ | $M_W$ 683 g/mol | |
| TLC Results: | $R_f$ | 0.15 | (hexane/ ethyl acetate 8:2) |
| | $R_f$ | 0.86 | (chloroform/ methanol 9:1) |

|  |  |  |  |
|---|---|---|---|
| | $R_f$ | 1.00 | (benzene/acetone/acetic acid 27:10:0.5) |
| HPLC Results: | $t_R$ | 55.11 | (20–80% B in 60 min Vydac C18) |
| FAB-MS: | [MH]$^+$ 684 | | |

Example 22

Synthesis of Fmoc—ValΨ[CH$_2$N(COCH$_2$CH$_2$NHAlloc)]Phe—OH

Fmoc—ValΨ[CH$_2$N(COCH$_2$CH$_2$NHAlloc)]Phe—OBu$^t$ (2.82 g) was treated with 90% TFA/water for 1 hour. After removing the TFA, the residue was washed with diethyl ether several times and then purified by flash-chromatography with chloroform/methanol (9:1) using silica gel 60 for column chromatography (particle size 0.040–0.063 mm).

|  |  |  |  |
|---|---|---|---|
| Yield: | 34% | | |
| | $C_{36}H_{41}N_3O_7$ | $M_W$ 627 g/mol | |
| | $[\alpha_D]^{25}$ | −51.60° (c = 1; methanol) | |
| TLC Results: | $R_f$: (S3) | 0.37 | |
| | $R_f$: (S6) | 0.13 | |
| HPLC Results: | $t_R$ | 42.46 | (20–80% B in 60 min Vydac C18) |
| FAB-MS: | [MH]$^+$ 628 | | |

Example 23

Synthesis of Fmoc—ValΨ[CH$_2$N(COCH$_2$CH$_2$COOAll)]Phe—OBu$^t$

Succinic anhydride (0.2 mol; 20.00 g), allyl alcohol (0.6 mol; 12.30 ml) and a catalytic amounts of DMAP were combined in 200 ml toluene and refluxed for 4 hours. The solvent and excessive allyl alcohol were removed by evaporation and the crude product was fractionated under vacuum.

|  |  |  |
|---|---|---|
| Yield: | 84% | |
| | $C_7H_{10}O_4$ | $M_W$ 158 g/mol |
| $K_p$: | 101° C. at 0.072 mbar | |
| FAB-MS: | [MH]$^+$ 159 | |

One equivalent succinic acid monoallylester (2 mmol; 0.316 g) was dissolved in dry THF and cooled to −15° C. One equivalent N-methyl morpholine (2 mmol; 0.22 ml) and 1 equivalent isobutyl chloroformate (2 mmol; 0.264 ml) were then added. After 10 minutes, a solution of 1 equivalent Fmoc—ValΨ[CH$_2$NH]Phe—OBu$^t$ (2 mmol; 1.056 g) and 1 equivalent N-methyl morpholine (2 mmol; 0.22 ml) in dry THF was added. The mixture was allowed to warm up gently to room temperature. After stirring overnight, the THF was removed and the residue dissolved in ethyl acetate, extracted with KHSO$_4$ (3×), NaHCO$_3$ (3×) and NaCl (3×). The organic phase was dried with Na$_2$SO$_4$ and the solvent was removed under vacuum to provide a yellow oil.

|  |  |  |  |
|---|---|---|---|
| Yield: | 95% (crude product) about 20% content | | |
| | $C_{40}H_{39}N_3O_7$ | $M_W$ 659 g/mol | |
| TLC Results: | $R_f$ | 0.31 | (hexane/ ethyl acetate 8:2) |
| | $R_f$ | 0.93 | (chloroform/ methanol 9:1) |
| | $R_f$ | 1.00 | (benzene/ acetone/ acetic acid 27:10:0.5) |
| HPLC Results: | $t_R$ | 58.54 | (20–80% B in 60 min Vydac C18) |
| FAB-MS: | [MH]$^+$ 660 | | |

Example 24

Synthesis of Fmoc—ValΨ[CH$_2$N(COCH$_2$CH$_2$COOAll)]Phe—OH

Fmoc—ValΨ[CH$_2$N(COCH$_2$CH$_2$COOAll)]Phe—OBu$^t$ (2.40 g) was treated with 90% TFA/water for 1 hour. After removing the TFA, the residue was washed with diethyl ether several times and then purified by flash-chromatography with chloroform/methanol (9:1) using silica gel 60 for column chromatography (particle size 0.040–0.063 mm).

|  |  |  |  |
|---|---|---|---|
| Yield: | 35% | | |
| | $C_{36}H_{40}N_2O_7$ | 612 g/mol | |
| | $[\alpha_D]^{25}$ | −49.9° | (c = 1; methanol) |
| TLC Results: | $R_f$: (S3) | 0.5 | |
| | $R_f$: (S6) | 0.18 | |
| HPLC Results: | $t_R$ | 45.25 | (20–80% B in 60 min Vydac C18) |
| FAB-MS: | [MH]$^+$ 613 | | |

Example 25

Synthesis of Fmoc—DPhe-Hydroxamate

One equivalent Fmoc—DPhe—OH (25.80 mmol; 10.00 g) and 1 equivalent N,O-dimethylhydroxylamine hydrochloride (28.38 mmol; 2.78 g) were dissolved in 100 ml THF, and the mixture was cooled to 0° C. To this were added 1.1 equivalents DIEA (28.38 mmol; 4.86 ml) and 1 equivalent N,N'-dicyclohexylcarbodiimid (25.80 mmol; 5.32 g), and stirring was continued at 0° C. for 1 hour and then at room temperature for 4 hours. The precipitating dicyclohexyl urea was filtered off and the solvent was removed under vacuum. The residue was dissolved in ethyl acetate and extracted with KHSO$_4$ (3×), NaHCO$_3$ (3×) and NaCl (3×). After drying with Na$_2$SO$_4$ and concentrating under vacuum, a wax-like substance was obtained. Remaining dicyclohexyl urea was separated using diethyl ether. The urea was filtered off and the solvent removed under vacuum.

|  |  |  |
|---|---|---|
| Yield: | 85% | |
| | $C_{26}H_{26}N_2O_4$ | $M_W$ 430 g/mol |
| TLC Results: | $R_f$: (S6) | 0.41 |

| HPLC Results: | $t_R$ | 40.52 | (20–80% B in 60 min Vydac C18) |
|---|---|---|---|
| FAB-MS: | [MH]⁺ 431 | | |

Example 26

Synthesis of Fmoc—DPhe—CHO

One equivalent Fmoc—DPhe-hydroxamate (23.23 mmol; 10.00 g) was dissolved in dry THF, and the solution was evacuated, covered with argon, and cooled to −15° C. 1.25 equivalents $LiAlH_4$ (29.04 mmol; 1.11 g) were then carefully added in portions. Stirring was continued at −15° C. for 15 min and then at room temperature for 1 hour. The mixture was then hydrolyzed with a concentrated solution of 1.75 equivalent $KHSO_4$ (40.65 mmol; 5.53 g). The THF was evaporated under vacuum. and the remaining aqueous solution was extracted with diethyl ether several times. The extracts were combined and extracted with $KHSO_4$ (3×), $NaHCO_3$ (3×) and NaCl (3×). After drying with $Na_2SO_4$ and concentrating under vacuum, an oil was obtained that was immediately used for further processing.

| Yield: | 60–80% | | |
|---|---|---|---|
| | $C_{24}H_{21}NO_3$ | $M_W$ 355 g/mol | |
| TLC Results: | $R_f$ | 0.16 | (hexane/ ethyl acetate 8:2) |
| | $R_f$ | 0.80 | (benzene/acetone/acetic acid 27:10:0.5) |
| | $R_f$ | 1 | (chloroform/ methanol 9:1) |
| HPLC Results: | $t_R$ | 35.57 | (20–80% B in 60 min Vydac C18) |
| FAB-MS: | [MH]⁺ 356 | | |

Example 27

Synthesis of Fmoc—DPheΨ[CH₂NH]Phe—OBu$^t$

One equivalent Phe—OBu$^t$HAc (11.42 mmol; 3.22 g) was treated with 1 equivalent triethylamine (11.42 mmol; 1.60 ml) and then added to a solution of 1 equivalent Fmoc—DPhe—CHO (11.42 mmol; 4.06 g) in dry methanol with molecular sieves. This mixture was stirred for 1 hour before being cooled to 0° C. 1.1 equivalents $NaCNBH_3$ (12.56 mmol; 0.70 g) were added in portions, and stirring was continued overnight. The molecular sieves were filtered off and methanol evaporated under vacuum. The residue was dissolved in ethyl acetate and extracted with $KHSO_4$ (3×), $NaHCO_3$ (3×) and NaCl (3×). After drying with $Na_2SO_4$ and concentrating under vacuum, a yellow oil was obtained.

| Yield: | 78% | | |
|---|---|---|---|
| | $C_{37}H_{40}N_2O_4$ | $M_W$ 576 g/mol | |
| TLC Results: | $R_f$: (S6) | 0.49 | |
| HPLC Results | $t_R$ | 43.98 | (20–80% B in 60 min Vydac C18) |
| FAB-MS: | [MH]⁺ 577 | | |

Example 28

Synthesis of Fmoc—DPheΨ[CH₂N (COCH₂CH₂NHAlloc)]Phe—OBu$^t$

One equivalent Alloc-β-Ala (2 mmol; 0.346 g) is dissolved in dry THF and cooled to −15° C. One equivalent N-methyl morpholine (2 mmol; 0.22 ml) and 1 equivalent isobutyl chloroformate (2 mmol; 0.264 ml) were then added. After 10 minutes, a solution of 1 equivalent Fmoc—DPheΨ[CH₂NH]Phe—OBu$^t$ (2 mmol; 1.152 g) and 1 equivalent N-methyl morpholine (2 mmol; 0.22 ml) in dry THF was added. The mixture was allowed to gently warm up to room temperature. After stirring overnight, the THF was removed and the residue dissolved in ethyl acetate, extracted with $KHSO_4$ (3×), $NaHCO_3$ (3×) and NaCl (3×). The organic phase was dried with $Na_2SO_4$ and the solvent removed under vacuum to provide a yellow oil.

| Yield: | 96% (crude product) about 31% content | | |
|---|---|---|---|
| | $C_{44}H_{49}N_3O_7$ | $M_W$ 731 g/mol | |
| TLC Results: | $R_f$ | 0.09 | (hexane/ ethyl acetate 8:2) |
| | $R_f$ | 0.85 | (chloroform/ methanol 9:1) |
| | $R_f$ | 1.00 | (benzene/acetone/acetic acid 27:10:0.5) |
| HPLC Results: | $t_R$ | 55.26 | (20–80% B in 60 min Vydac C18) |
| FAB-MS: | [H]⁺ 732 | | |

Example 29

Synthesis of Fmoc—DPheΨ[CH₂N (COCH₂CH₂NHAlloc)]Phe—OH

Fmoc—DPheΨ[CH₂N(COCH₂CH₂NHAlloc)]Phe—OBu$^t$ (2.275 g) is treated with 90% TFA/water for 1 hour. After removing the TFA, the residue was washed with diethyl ether several times and purified by flash-chromatography with chloroform/methanol (9:1) using silica gel 60 for column chromatography (particle size 0.040–0.063 mm).

| Yield: | 38% | | |
|---|---|---|---|
| | $C_{40}H_{41}N_3O_7$ | $M_W$ 675 g/mol | |
| | $[\alpha_D]^{25}$ | −32.6° | (c = 1; methanol) |
| TLC Results: | $R_f$: (S3) | 0.48 | |
| | $R_f$: (S6) | 0.25 | |
| HPLC Results: | $t_R$ | 43.25 | (20–80% B in 60 min Vydac C18) |
| FAB-MS: | [MH]⁺ 676 | | |

Example 30

Synthesis of Fmoc—DPheΨ[CH₂N (COCH₂CH₂COOAll)]Phe—OBu$^t$

Succinic anhydride (0.2 mol; 20.00 g), allyl alcohol (0.6 mol; 12.30 ml) and a catalytic amounts of DMAP in 200 ml toluene were refluxed for 4 hours. The solvent and excessive allyl alcohol were removed and the crude product fractionated under vacuum.

| | | | |
|---|---|---|---|
| Yield: | 84% | | |
| | $C_7H_{10}O_4$ | | $M_W$ 158 g/mol |
| $K_p$: | 101° C. at 0.072 mbar | | |
| FAB-MS: | $[MH]^+$ 159 | | |

One equivalent succinic acid monoallylester (2 mmol; 0.316 g) was dissolved in dry THF and cooled to −15° C. One equivalent N-methyl morpholine (2 mmol; 0.22 ml) and 1 equivalent isobutyl chloroformate (2 mmol; 0.264 ml) are added. After 10 min a solution of 1 equivalent Fmoc—DPheΨ[$CH_2NH$]Phe—$OBu^t$ (2 mmol; 1.152 g) and 1 equivalent N-methyl morpholine (2 mmol; 0.22 ml) in dry THF were then added. The mixture was allowed to warm up gently to room temperature. After stirring overnight, the THF was removed and the residue was dissolved in ethyl acetate, extracted with $KHSO_4$ (3×), $NaHCO_3$ (3×) and NaCl (3×). The organic phase is dried with $Na_2SO_4$ and the solvent was removed under vacuum to provide a yellow oil.

| | | | |
|---|---|---|---|
| Yield: | 92% | | |
| | (crude product) | | |
| | about 27% content | | |
| | $C_{44}H_{48}N_2O_7$ | $M_W$ 716 g/mol | |
| TLC Results: | $R_f$ | 0.20 | (hexane/ ethyl acetate 8:2) |
| | $R_f$ | 0.93 | (chloroform/ methanol 9:1) |
| | $R_f$ | 1.00 | (benzene/ acetone/ acetic acid 27:10:0.5) |
| HPLC Results: | tR | 58.67 | (20–80% B in 60 min Vydac C18) |
| FAB-MS: | $[H]^+$ 717 | | |

Example 31

Synthesis of Fmoc—DPheΨ[$CH_2N$($COCH_2CH_2COOAll$)]Phe—OH

Fmoc—DPheΨ[$CH_2N(COCH_2CH_2COOAll)$]Phe—$OBu^t$ (2.19 g) was treated with 90% TFA/water for 1 hour. After removing the TFA, the residue was washed with diethyl ether several times and purified by flash-chromatography with chloroform/methanol (9:1) using silica gel 60 for column chromatography (particle size 0.040–0.063 mm).

| | | | |
|---|---|---|---|
| Yield: | 36% (727 mg) | | |
| | $C_{40}H_{40}N_2O_7$ | $M_W$ 660 g/mol | |
| | $[\alpha_D]^{25}$ | −23.5° | |
| | | (c = 1; methanol) | |
| TLC Results: | $R_f$: (S3) | 0.55 | |
| | $R_f$: (S6) | 0.27 | |
| HPLC Results | $t_R$ | 46.00 | (20–80% B in 60 min Vydac C18) |
| FAB-MS: | $[MH]^+$ 661 | | |

While the present invention has been described with respect to the particular embodiments and examples provided above, it will be apparent to those skilled in the art that various changes and modifications may be made without departing from the spirit and scope of the invention as defined in the claims. Such modifications are intended to fall within the scope of the appended claims.

What is claimed is:

1. A building unit of the formula:

$$X-AA_m-\Psi(C^\alpha H_2N)[CO(CH_2)_qW]-AA_p-Y$$

wherein $AA_m$ and $AA_p$ are residues of natural or synthetic amino acids; N is the nitrogen atom of the N-terminus residue of $AA_p$; $C^\alpha$ is the a carbon atom of $AA_m$ if m>0 with respect to N; W is NH—X or COY; X is selected from the group consisting of H, Boc, Z, Fmoc, and Alloc; Y is the hydroxyl group of a carboxylic acid moiety or a carboxylic acid protecting group; m is a number from 0 to 10; p is a number from 1 to 10; and q is a number from 1 to 6.

2. The building unit of claim 1, wherein $AA_m$ and $AA_n$ each comprises one or more residues of an amino acid selected from the group consisting of D—Phe, Phe, D—Val, and Val; and Y is selected from the group consisting of hydroxyl, alkoxy, substituted alkoxy, allyloxy; substituted allyloxy, aryloxy, substituted aryloxy, and trimethylsilyl ether.

3. The building unit of claim 2, wherein X is selected from the group consisting of H, Boc, Z, Fmoc, and Alloc; and Y is selected from the group consisting of OMe, OEt, $OBu^t$, OBzl, and Allyl.

4. The building unit of claim 1, wherein m is a number from 1 to 4; p is a number from 1 to 4, and q is a number from 1 to 4.

5. The building unit of claim 1, wherein $AA_m$ and $AA_p$ each comprises one or more residues of an amino acid selected from the group consisting of D—Phe, Phe, D—Val, and Val.

6. The building unit of claim 1, wherein Y is selected from the group consisting of hydroxyl, alkoxy, substituted alkoxy, allyloxy, substituted allyloxy, aryloxy, substituted aryloxy, and trimethylsilyl ether.

7. The building unit of claim 1, wherein Y is selected from the group consisting of OMe, OEt, $OBu^t$, OBzl, and Allyl.

8. The building unit of claim 1, wherein m is a number from 1 to 4.

9. The building unit of claim 1, wherein p is a number from 1 to 4.

10. The building unit of claim 2, wherein q is a number from 1 to 4.

11. A building unit selected from the group consisting of:
Fmoc—ValΨ[$CH_2$—N(CO—$CH_2$—$CH_2$—NHBoc)]Phe;
Z—ValΨ[$CH_2$—N(CO—$CH_2$—$CH_2$—NHBoc)Phe—OBzl;
H—ValΨ[$CH_2$—N(CO—$CH_2$—$CH_2$—NHBoc)]Phe—OH;
Fmoc—ValΨ[$CH_2N(COCH_2CH_2NHAlloc)$]Phe—$OBu^t$;
Fmoc—ValΨ[$CH_2N(COCH_2CH_2NHAlloc)$]Phe—OH;
Fmoc—ValΨ[$CH_2N(COCH_2CH_2COOAll)$]Phe—$OBu^t$;
Fmoc—ValΨ[$CH_2N(COCH_2CH_2COOAll)$]Phe—OH;
Fmoc—DPheΨ[$CH_2N(COCH_2CH_2NHAlloc)$]Phe—$OBu^t$;
Fmoc—DPheΨ[$CH_2N(COCH_2CH_2NHAlloc)$]Phe—OH;
Fmoc—DPheΨ[$CH_2N(COCH_2CH_2COOAll)$]Phe—$OBu^t$; and
Fmoc—DPheΨ[$CH_2N(COCH_2CH_2COOAll)$]Phe—OH.

* * * * *

UNITED STATES PATENT AND TRADEMARK OFFICE
CERTIFICATE OF CORRECTION

PATENT NO. : 6,184,345 B1
DATED : February 6, 2001
INVENTOR(S) : Siegmund Reissmann et al.

It is certified that error appears in the above-identified patent and that said Letters Patent is hereby corrected as shown below:

Column 30,
Line 11, change "a" to -- $\alpha$ --, and after "M>0" insert -- , --. Line 11 should now read as follows: "residue of AA$_p$; C$^\alpha$ is the $\alpha$ carbon atom of AA$_m$ if m>0, with".
Line 50, after "NHBoc)" insert -- ] --. Line 50 should now read as follows:
"Z—Val$\Psi$[CH$_2$—N(CO—CH$_2$—CH$_2$—NHBoc)]Phe —".

Signed and Sealed this

Fourth Day of December, 2001

Attest:

*Nicholas P. Godici*

NICHOLAS P. GODICI
*Attesting Officer*  *Acting Director of the United States Patent and Trademark Office*